United States Patent [19]

Cree

[11] Patent Number: 4,850,996

[45] Date of Patent: Jul. 25, 1989

[54] SAFETY NEEDLE

[76] Inventor: Ian C. Cree, P.O. Box 610, Shelburne N.S., Canada, B0T1W0

[21] Appl. No.: 158,627

[22] Filed: Feb. 22, 1988

[51] Int. Cl.⁴ ............................................. A61M 5/32
[52] U.S. Cl. ................................. 604/198; 604/192; 604/263
[58] Field of Search ............... 604/110, 162, 192, 197, 604/198, 263

[56] References Cited

U.S. PATENT DOCUMENTS

| | | | |
|---|---|---|---|
| 2,674,246 | 4/1954 | Bower | 604/198 |
| 2,876,770 | 3/1959 | White | 604/198 |
| 3,356,089 | 12/1967 | Francis | 604/197 |
| 4,416,663 | 11/1983 | Hall | 604/198 |
| 4,417,887 | 11/1983 | Koshi | 604/162 |
| 4,507,118 | 3/1985 | Dent | 604/198 |
| 4,636,201 | 1/1987 | Ambrose et al. | 604/192 |
| 4,639,249 | 1/1987 | Larson | 604/198 |
| 4,642,099 | 2/1987 | Phillips et al. | 604/198 |
| 4,660,570 | 4/1987 | Dombrowski | 604/198 |
| 4,664,654 | 5/1987 | Strauss | 604/198 |

FOREIGN PATENT DOCUMENTS

| | | | |
|---|---|---|---|
| 0268445 | 5/1988 | European Pat. Off. | 604/198 |
| 2079607 | 1/1982 | United Kingdom | 604/198 |

Primary Examiner—Max Hindenburg
Assistant Examiner—K. M. Reichle
Attorney, Agent, or Firm—Charmasson & Holz

[57] ABSTRACT

A sheath is provided as a cover over a hollow needle for use by medical personnel in combination with a syringe. When needle is not in use, the sheath protects medical personnel from accidental scraping or injections. During use in injections, the sheath is retracted by skin contact into a chamber attached to the proximal end of the needle. The sheath can also be capped or sealed when not in use to maintain safe conditions until actual injection use on a patient. The sheath may also be restrained from retraction during shipping or rough handling. The sheath is made from transparent material to not impede accurate injection of the needle into the patient. In use, the sheath further maintains sterile conditions at the point of injection by precluding airborne contamination.

8 Claims, 2 Drawing Sheets

SAFETY NEEDLE

FIELD OF THE INVENTION

This invention relates to medical equipment, more specifically to medical needles and associated caps/covers.

BACKGROUND OF THE INVENTION

The hollow, pointed stainless steel needle, attached to a syringe is a standard medical method of giving injections or withdrawing body fluids. Injections (or withdrawals) can be given under (hypodermic or subcutaneous) or into (intradermal) the skin, veins (intravenous) or muscles (intramuscular). Because of the sharp pointed end, plastic caps are usually supplied with the medical needle to prevent injury and maintain sterile conditions. After use, the needle may be recapped for future sterilization and reuse or disposed of. Recapping may still be required to prevent injury, even if the needle is to be disposed of.

Even though care is exercised, accidental injury from needles occurs. The process of capping and recapping can cause scratches or needle insertions just by brushing against the sharp point. Uncovering the needle is also typically accomplished before use, so that needle accidents may occur in the interim between uncovering and use.

The time for accidental penetration between use and recapping of the needle is even more serious. The patient from which the needle was extracted, may have a communicable disease, or a disease transmitted by penetration of contaminated fluids into the tissues of healthy persons. The current AIDS epidemic has focused attention on this risk. Health care workers are especially exposed to this risk. In an emergency room environment, the health care worker may be distracted while recapping the needle, thereby exposing the worker and nearby personnel to injury and infection.

SUMMARY OF THE INVENTION

The principal and secondary objects of this invention are:

to provide a hollow medical needle sheath which exposes the sharp point only during use;

to provide a needle sheath which covers the sharp point immediately upon extracting the needle; and to provide a positive means to maintain the sheath in place and the sterile condition of the needle prior to use.

These and other objects are achieved by providing a latched, spring-activated cylindrical sheath around the needle. The end of the sheath proximate the patient extends beyond needle point, and has a lip. Pressing against the lip compresses the spring once the latch is removed, allowing the needle to be inserted into the patient. Upon removal, the spring returns the sheath to the covered position where it is again latched into position. A disposable cover maintains the sterile condition of the assembly prior to use.

DESCRIPTION OF THE PREFERRED EMBODIMENT OF THE INVENTION

Figure 1:
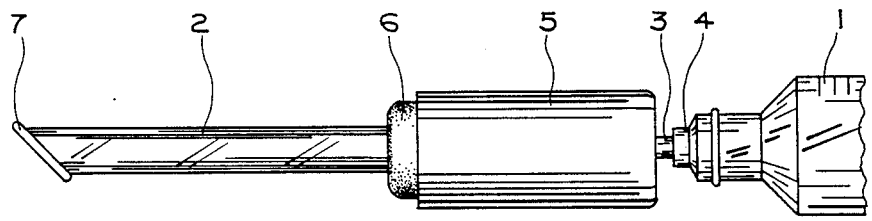
FIG. 1 is a side view of a safety needle.

FIG. 1 shows a side view of a safety needle for use with a syringe 1. A sheath 2 extends beyond the tip of needle 3. A female syringe coupling 4 is attached to the opposite end of the needle 3. A sheath chamber 5 is attached to needle 3 proximate to female syringe coupling 4. Cap hub 6 is attached to chamber 5 proximate the sharp point of needle 3 (not shown in this view). Sheath 2 is slidably mounted into the chamber 5.

Figure 2:
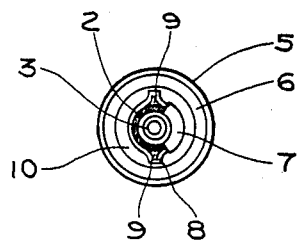
FIG. 2 is a front view of a safety needle.

FIG. 2 is a front view of a safety needle. Sheath chamber 5 encloses hollow needle 3, except for frontal openings (between needle 3 and sheath 2, and between sheath 2 and rim 10) and the portion of needle extending to the female syringe coupling 4 (see FIG. 1). Cap hub 6 on the distal end of chamber 5 includes cutouts 8. These cutouts allow assembly of sheath 2 which includes lip segments 9. After assembly lip segments 9 are rotated to rest against the inwardly flanged rim 10 of the chamber.

Figure 3:
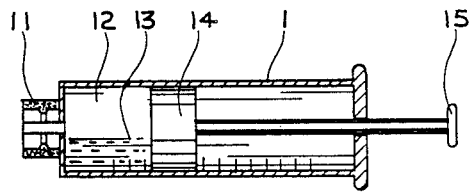
FIG. 3 is a side view of a syringe.

FIG. 3 is a side cross-sectional view of a syringe 1. Male syringe coupling 11 is attached to the end of syringe cavity 12, which contains the fluid 13 to be injected into or withdrawn from the patient. Plunger 14 traverses the interior of the syringe cavity 12, displacing or drawing fluid 13. Motion is induced by manual displacement of tip 15.

Figure 4:
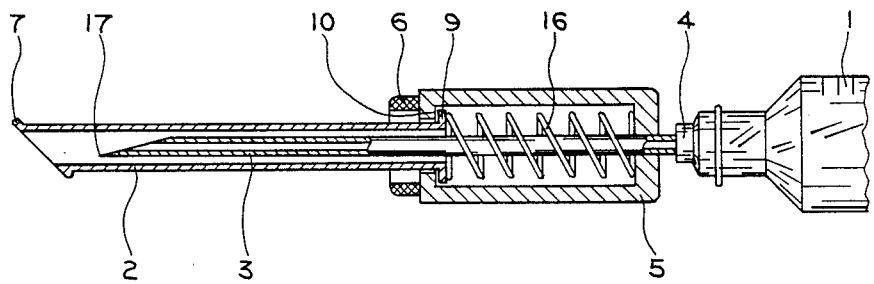
FIG. 4 is a cross-sectional side view of a safety needle with extended sheath.

FIG. 4 shows a side cross-section of the safety needle. Female syringe coupling is bonded to one end of hollow needle 3, typically made from surgical steel. A cylindrical sheath cavity or chamber 5 is welded or adhesively bonded near the proximate end of the needle 3 proximate to the female syringe coupling. A spring 16 is placed within the cavity 5 surrounding needle 3. The spring 16 is biasing lip segments 9 of sheath 2 away from the bonded proximal end of sheath cavity 5. Sheath 2 extends from chamber 5 to beyond sharp needle point 17 of needle 3. Sheath end 7 is enlarged in diameter to provide an extended area or lip to press against when sheath is depressed. Cap hub 6 is bonded and supported by sheath chamber 5 ends, which also provide a stop to the outward travel of sheath 2.

Figure 5:
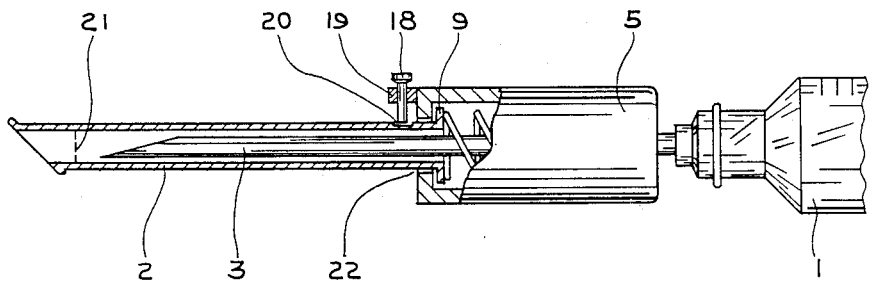
FIG. 5 is a cross-sectional side view of a latched safety needle.

FIG. 5 is a side cross-section of an alternate safety needle. Configuration is identical to FIG. 4 except that the cap hub 6 has been removed and a retainer 18, retainer holder 19, needle detent 20 and foil seal 21 have been provided. Retainer 18 is slidably mounted on retainer holder 19, which is bonded to the distal open end of sheath chamber 5. When retainer 18 is biased diametrically inward against needle detent 20 or sufficient friction prevents retraction from detent 20, sheath 2 is prevented from travel. If lip segments 9 are continuous around circumference of sheath 2 and seal the open end 22 of sheath chamber 5, the addition of foil 21 (shown dotted) can complete the sealing of the insertable portion of needle 3. This sealing would maintain sterile conditions until foil seal was removed or punctured.

Foil seal 21 location may be located anywhere beyond the end of needle 3. A cap over the distal end of sheath 2 would be an alternate method of sealing.

Figure 6:
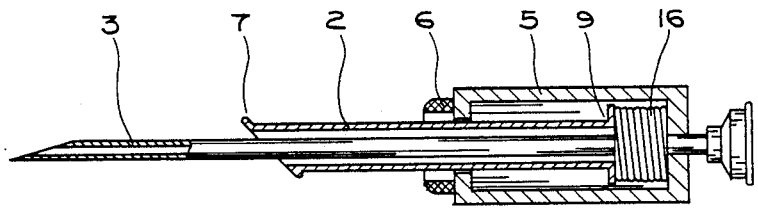
FIG. 6 is a cross-sectional side view of a safety needle with a compressed sheath.

FIG. 6 is a side cross-section of a safety needle with a depressed sheath. Lip segments 9 compress spring 16 within cavity 5 when force is exerted on distal end of sheath 2. Depression of spring 16 and sheath 2 exposes needle 2 for use. Cap hub 6 is unaffected by sheath travel.

Figure 7:
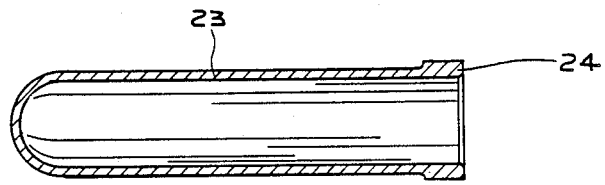
FIG. 7 is a cross-sectional side view of a cap.

FIG. 7 shows a side cross-section of a cap. Cylindrical cap 23 is long enough and wide enough in diameter to enclose needle 3 and sheath 2 when attached to cap hub 6 (see FIG. 9). Cap hub coupling 24 attaches to cap hub 6 (not shown for clarity).

Figure 8:
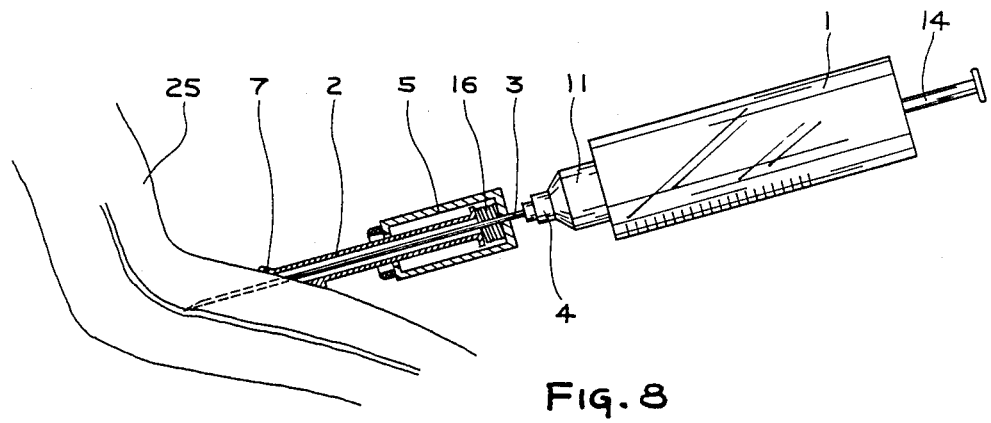
FIG. 8 is a cross-sectional side view of a syringe and needle.

FIG. 8 is a cross-sectional side view of safety needle in use. Skin of patient's 25 is used to depress sheath 2, exposing needle 3 which is inserted into patient 25 (insertion shown dotted). Complete depression of spring 16 is not required, and sheath 2 forms a barrier to airborne contamination during insertion and withdrawal. Sheath resting on pateint 25 also steadies the needle 3. If sheath 2 is made of transparent plastic material, no loss of insertion accuracy occurs. Rounded sheath end 7 provides a comfortable area for skin contact. Once needle 3 is inserted into patient's skin 25, syringe plunger 14 is manually actuated to withdraw or inject fluid into/from syringe 1. Male syringe coupling 11 provides the leak-free attachment to female syringe coupling 4.

Figure 9:
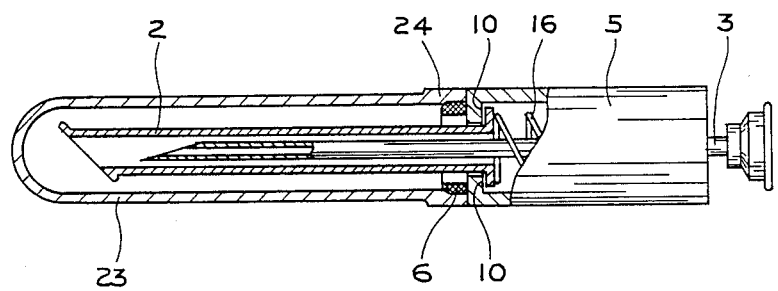
FIG. 9 is a cross-sectional side view of needle and cap.

FIG. 9 shows a cross-sectional side view of a capped safety needle. Cap 23 is attached to sheath chamber 5 by cap hub coupling 24 and cap hub 6. The coupling and cap provides a sealed volume to maintain cleanliness and further protect against accidental injury from needle 3. Sheath 2 and spring 16 are shown in the extended position.

While the preferred embodiments of the invention have been described, and modifications thereto have been suggested, it should be understood that other applications and modifications could be made without departing from the spirit of the invention and the scope of the appended claims.

What is claimed is:

1. In combination with a syringe
   containing a fluid for injection into a patient, a safety needle which comprises:
   a hollow generally cylindrical needle allowing passage of said fluid, attached at one end to said syringe, having the other end shaped to penetrate the patient's skin;
   a safety needle cover comprising:
   a tubular chamber coaxial with, and surrounding but spaced apart from a portion of said needle, said chamber having a closed proximate end attached to said needle proximate, but spaced from the one end of said needle and a distal end spaced from the other end of the needle and forming a concentric opening therearound to the interior of said chamber;
   a tubular translating sheath, one end proximate said chamber, and the other end extending beyond the other end of said needle in a first position;
   means for slidably engaging said one end of said sheath to said chamber, said engaging means slidably engaging said one end of said sheath such that said sheath is capable of translating upon contact with the patient from the first position to a second position wherein a portion of said sheath moves with respect to said chamber to expose the other end of said needle;
   means for biasing said sheath toward said first position; and
   wherein said safety needle cover is only directly attached to said needle and thereby, separate from said syringe.

2. The combination claimed in claim 1, wherein said means for biasing consists of a coiled spring, acting between the closed end of said chamber and the one end of said translating sheath.

3. The combination claimed in claim 2 which further comprises:
   a cap hub attached to said distal end of said chamber; and
   a cap attachable to said cap hub, said cap shaped and dimensioned to cover and seal said sheath and said opening of said chamber.

4. The combination claimed in claim 3 which further comprises a means for retaining said sheath in one position.

5. The combination claimed in claim 4, wherein said means for retaining consists of a detent in said sheath, a retainer shaped and dimensioned to restrain said sheath when inserted into said detent, and a retainer holder attached to said chamber slidably attached to said retainer.

6. The combination claimed in claim 5, wherein said chamber and sheath are made from materials that may be sterilized prior to use with the patient.

7. The combination claimed in claim 6, wherein said materials are transparent.

8. The combination claimed in claim 1 which further comprises:
   a foil seal spanning the interior of said sheath between its other end and the other end of said needle.

* * * * *